(12) United States Patent
Buresh, II et al.

(10) Patent No.: US 9,657,893 B2
(45) Date of Patent: May 23, 2017

(54) CLIP FOR A PATIENT MONITORING POD

(71) Applicant: Draeger Medical Systems, Inc., Andover, MA (US)

(72) Inventors: William T. Buresh, II, Salem, NH (US); Timothy Joseph Coonahan, Sterling, MA (US); Rajesh Rane, Cambridge, MA (US); Stanley Thompson, Andover, MA (US); Ken Zhen, Lincoln, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 172 days.

(21) Appl. No.: 14/414,426

(22) PCT Filed: Jul. 12, 2013

(86) PCT No.: PCT/US2013/050384
§ 371 (c)(1),
(2) Date: Jan. 12, 2015

(87) PCT Pub. No.: WO2014/012064
PCT Pub. Date: Jan. 16, 2014

(65) Prior Publication Data
US 2015/0204699 A1 Jul. 23, 2015

Related U.S. Application Data

(63) Continuation-in-part of application No. 29/427,118, filed on Jul. 13, 2012, now Pat. No. Des. 741,161.

(60) Provisional application No. 61/807,551, filed on Apr. 2, 2013, provisional application No. 61/682,144, filed on Aug. 10, 2012, provisional application No. 61/671,576, filed on Jul. 13, 2012.

(51) Int. Cl.
| | |
|---|---|
| F16M 13/02 | (2006.01) |
| F16M 11/04 | (2006.01) |
| F16M 13/00 | (2006.01) |
| F16M 13/04 | (2006.01) |
| A61B 5/00 | (2006.01) |

(52) U.S. Cl.
CPC ........ *F16M 13/022* (2013.01); *F16M 11/041* (2013.01); *F16M 13/005* (2013.01); *F16M 13/04* (2013.01); *A61B 5/6838* (2013.01); *Y10T 24/44316* (2015.01); *Y10T 24/44402* (2015.01)

(58) Field of Classification Search
CPC ..................................................... F16M 13/005
See application file for complete search history.

(56) References Cited

U.S. PATENT DOCUMENTS 5,219,139 A * 6/1993 Hertzler .................. A61G 5/10
248/276.1
6,029,871 A 2/2000 Park
(Continued)

OTHER PUBLICATIONS

"BIS VISTA™ Monitoring System: Service Information Manual." Aspect Medical Systems, Inc. (2009):1-98.
(Continued)

*Primary Examiner* — Ryan Walsh
(74) *Attorney, Agent, or Firm* — Jones Day

(57) ABSTRACT

Disclosed are clips for a patient monitoring pod that is used with portable patient monitoring devices and systems. A patient monitoring pod and clip can rotate relative to each other to accommodate a patient's environment.

20 Claims, 19 Drawing Sheets

(56) References Cited

U.S. PATENT DOCUMENTS

2003/0106917 A1 6/2003 Shetler et al.
2004/0069821 A1 4/2004 Kobayashi

OTHER PUBLICATIONS

International Search Report and Written Opinion issued in PCT/US2013/050384 on Feb. 19, 2014.

* cited by examiner

CLIP FOR A PATIENT MONITORING POD

RELATED APPLICATIONS

This application is a National Stage Application under 35 U.S.C. 371 of PCT application PCT/US2013/050384, titled, "Clip for a Patient Monitoring Pod," filed Jul. 12, 2013, which in turn claims priority to U.S. Provisional Application No. 61/671,576, titled, "Clip For A Patient Monitoring Pod," filed Jul. 13, 2012; U.S. Provisional Application No. 61/682,144, titled, "Clip For A Patient Monitoring Pod," filed Aug. 10, 2012; U.S. Provisional Application No. 61/807,551, titled, "Clip For A Patient Monitoring Pod," filed Apr. 2, 2013 and U.S. Design patent application No. 29/427,118, titled, "Clip for a Patient Monitoring Pod," filed Jul. 13, 2012. The disclosures of the aforementioned applications are hereby incorporated by reference in their entireties herein.

TECHNICAL FIELD

The subject matter described herein relates generally to the field of medical devices, and more particularly to devices, systems, articles, and methods used to improve the monitoring of a patient, specifically a patient who changes locations.

BACKGROUND

Patient monitoring systems enable a physician or other caregiver to be aware of a condition of a patient. In a hospital setting, patients can be moved from one location to another. In such situations, it can be cumbersome to detach a patient from one or more monitoring devices at a first location and attach him or her to monitoring devices at a second location. Some patient monitoring systems are capable of being moved to accommodate changes in patient location in a hospital or other care facility. Other patient monitoring systems are capable of having patient monitoring components, or pods, changed out according to the status of the patient as well as his or her location.

SUMMARY

Provided herein is a clip for attaching a patient monitoring module, or pod, to a rod, pole, stand, or patient monitoring device, in which the clip includes a base plate with an interface on one side and a spring attached to a lever arm and clamp on the reverse side.

In some implementations, provided herein is a clip for attaching a medical device to a structure that includes a base portion and a lever arm. The base portion includes a rotating interface portion, an interface fitting to interface with the medical device, the interface fitting operably connected to the rotating interface portion; a locking mechanism to lock the interface fitting to the medical device; and a lock release to release the locking mechanism from the medical device. The lever arm includes a user grasping area, a clamp, and a torsion spring that provides torsion to the connection with the base portion.

The following features can be present in the clip in any suitable combination. In some implementations, the interface fitting of the base portion of the clip can be a sliding interface fitting. The interface fitting can be a snap on fitting in some implementations of the clip. The clip can include one or more friction pads in some implementations. In such implementations, the one or more friction pads can be located on opposed, facing portions of the clamp, at the portion of the clamp that is configured to contact the structure. In some implementations of the clip, the structure can include a shelf, a rod, a bed, or any combination thereof. The clip can also include a rotation mechanism that allows the rotating interface portion to rotate on the base portion, the rotation mechanism that includes at least one ball, a spring, and at least one detent. The clip can further include comprising a rotation mechanism that allows the rotating interface portion to rotate on the base portion, the rotation mechanism that includes a latch arm and a latch pin in some implementations. In some implementations, the clip can be configured to rotate in discrete increments. The clip can be configured to rotate in any convenient amount. The locking mechanism of the clip can be configured to release the medical device only when the rotating interface portion is in a specific position with respect to the clip base portion in some implementations. In some implementations of the clip, the base portion can be a plate.

In a related aspect, provided herein is a patient monitoring pod that includes a first face and a second face that are substantially parallel to each other, a mount block in a portion of the first face, and a recessed fitting on the second face.

The following features can be present in the patient monitoring pod in any suitable combination. In some implementations, the mount block can include a protrusion comprising a base and an interfacing portion, the interfacing portion being larger than the base of the protrusion, such that there is an undercut into which a receiving interface mechanism can fit. The receiving interface mechanism can include the interface fitting of a clip, clamp and vise fittings, or a recessed fitting on a second face of a second patient monitoring pod. In some implementations, the types of reading that the patient monitoring pod can take includes blood pressure, respiration rate, oxygen saturation, temperature, heart rate, and any combination thereof. The patient monitoring pod can be configured to stack with other, similar patient monitoring pods that interface via a mount block and recessed fitting in each patient monitoring pod.

Further, in a related aspect, provided herein is a method that includes providing a patient monitoring pod and clip assembly that includes a patient monitoring pod and a clip that is configured to releasably connect to the patient monitoring pod, as well as providing sensors configured to provide data to the patient monitoring pod and to monitor the patient's blood pressure, respiration rate, oxygen saturation, temperature, heart rate, or any combination thereof. The clip includes a base portion comprising a rotating interface portion; a lever arm connected with the base portion, the lever arm having a first end and a second end; a user grasping area at the first end of the lever arm; a clamp at the second end of the lever arm; and a torsion spring that provides torsion to the connection with the base portion. The base portion also includes an interface fitting to interface with the patient monitoring pod, the interface fitting operably connected to the rotating interface portion; a locking mechanism to lock the interface fitting to the patient monitoring pod; and a lock release to release the locking mechanism from the patient monitoring pod.

The following features can be present in the method in any suitable combination. The method can also include rotating the patient monitoring pod to accommodate a patient's position relative to the patient monitoring pod in some implementations. The rotating interface portion can include a rotating mechanism that comprises at least one ball, a spring, and at least one detent in some implementations. In some implementations, the rotating interface portion comprises a rotating mechanism that comprises a latch arm and a latch pin.

In a related aspect, provided herein is a clip for attaching a medical device to a structure that includes a lever arm that includes a user grasping area and a clamp; a base portion in a position opposed to the lever arm and connected to the lever arm via a torsion spring; a rotation mechanism configured to restrict rotation of the base portion with respect to the medical device; and a mounting block to interface with the medical device, the mounting block operably connected to the latch base of the rotation mechanism. The torsion spring provides torsion between the lever arm and the base portion. The rotation mechanism includes a latch arm attached at first end to the base portion and free at second end; a latch pin configured to sit in the second end of the latch arm; and a latch base operably connected to the base portion, the latch base configured to accept the latch pin.

The following features can be present in the clip for attaching a medical device to a structure in any suitable combination. In some implementations, the latch base can include notches that are configured to allow for immobilization of the latch pin and movement of the latch pin in and out of each notch. The latch arm can be configured to move the latch pin. In some implementations, the base portion can be shaped to accept the latch arm when pressure applied by a user on the latch arm causes the latch arm to move towards the base portion. In some implementations of the clip, moving the latch arm towards the base portion can allow for rotation of the latch base. In such implementations, moving the latch arm towards the base portion can move the latch pin into a position that may not impeded the rotation of the latch base.

The details of one or more variations of the subject matter described herein are set forth in the accompanying drawings and the description below. Other features and advantages of the subject matter described herein will be apparent from the description and drawings, and from the claim.

DESCRIPTION OF DRAWINGS

Like reference symbols in the various drawings indicate like elements.

DETAILED DESCRIPTION

Disclosed herein are clips for attaching patient monitoring pods, or self-contained modules, that are portable and that can be used with various types of connectors to patient monitoring devices, portable structures, or stationary structures. The clips allow for long-term or short-term attachment of a patient monitoring pod to a clip. A short-term attachment fitting allows a user to mount a clip to a difficult location on a structure and then interchange the patient monitoring pod as needed. Conversely, a long-term attachment fitting allows for a robust connection, in which the clip position can be changed as needed without excessive concern from the user about the stability of the location of the patient monitoring pod. The patient monitoring pods are also disclosed herein in so far as how the pods can attach to the clips and to other pods.

The clips for use with patient monitoring pods disclosed herein can allow a patient monitoring pod to rotate with respect to a clip affixed to a rail, pole, or other structure. Though this rotation is described below in discrete increments of 90 degrees, this rotation can include increments of less than 90 degrees, greater than 90 degrees, or an arbitrary rotation. One of the advantages of the ability to rotate the patient monitoring pod relative to the clip is that cable and cord routing from the patient monitoring pod to the patient and/or monitoring device can be simplified. Another advantage of this ability to rotate the patient monitoring pod relative to the clip is that the assembly can adapt to more locations around a patient's bed. Accordingly, the clip can attach to a bed rail, a shelf or ledge near a patient's bed, or onto a rack or pole used for other equipment that is near a patient, and the patient monitoring pod can be turned to a convenient orientation about the clip because of this ability to rotate.

Patient monitoring devices that can be used with the patient monitoring pods and clips described herein are described in more detail in U.S. Provisional Patent Application No. 61/635,372, U.S. Design patent application No. 29/424,360, and U.S. Design patent application No. 29/379, 086 the disclosures of which are hereby incorporated herein in their entireties.

Patient monitoring pods that are described as compatible with the clips disclosed herein are described in more detail in U.S. Provisional Patent Application No. 60/947,046, U.S. patent application Ser. No. 12/165,067, and U.S. patent application Ser. No. 11/961,071, the disclosures of which are hereby incorporated herein in their entireties.

Patient Monitoring Pod and Clip Assembly

Figure 1:
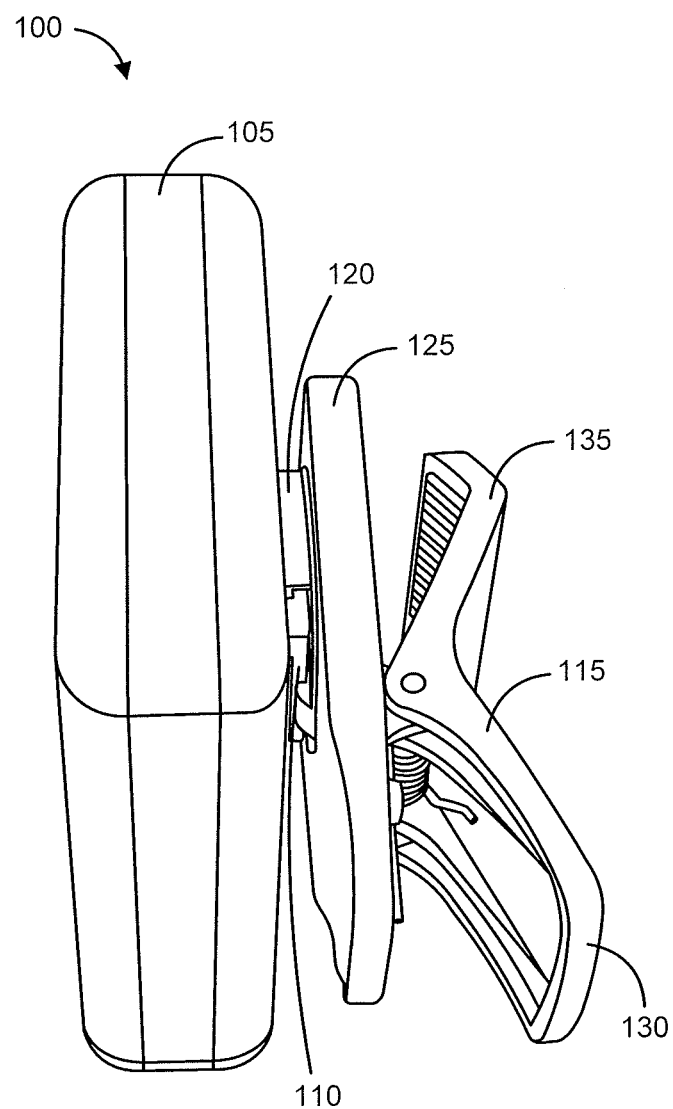
FIG. 1 shows a patient monitoring pod attached to a clip.

FIG. 1 illustrates a patient monitoring pod and clip assembly 100. The patient monitoring pod and clip assembly 100 includes a patient monitoring pod 105, with a mount block 110 on one large face, and a clip 115 that attaches to the patient monitoring pod 105 at an interface 120. The clip 115 has a base portion 125 that is attached to the interface 120, and on the side of the base portion 125 opposite the interface is the top portion of the clip that includes the lever arm 130 and the clamp 135.

Figure 2:
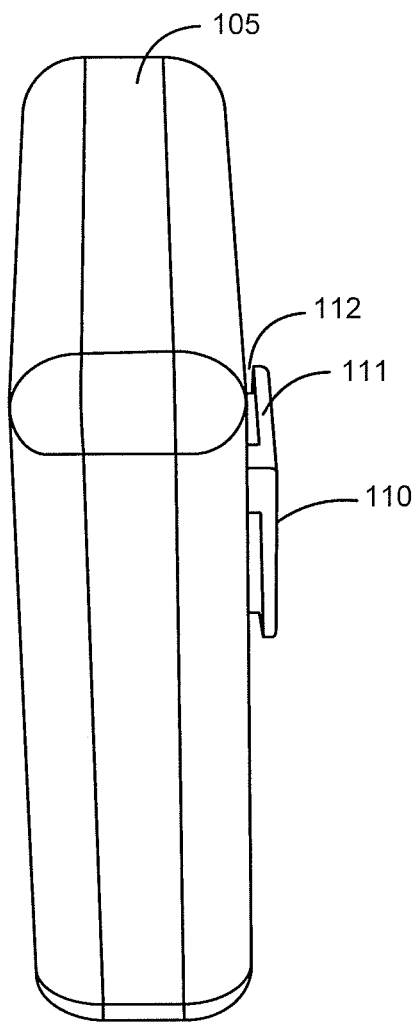
FIG. 2 the patient monitoring pod shown in FIG. 1 without the clip attached.

FIG. 2 shows the patient monitoring pod 105 shown in FIG. 1 without the clip attached. The patient monitoring pod 105 shown here has two substantially square faces that are parallel to each other. The mount block 110 lies in the center of one of the square faces. The mount block 110 is a protrusion that has an interfacing portion 111 that is larger than the base of the protrusion, such that there is an undercut 112 into which a receiving interface mechanism can fit. The mount block 110 of the patient monitoring pod 105 can fit into the clips described herein as well as into existing mounting mechanisms including clamp and vise fittings. Further described herein are patient monitoring pods which can receive a mount block from another patient monitoring pod.

Figure 3:
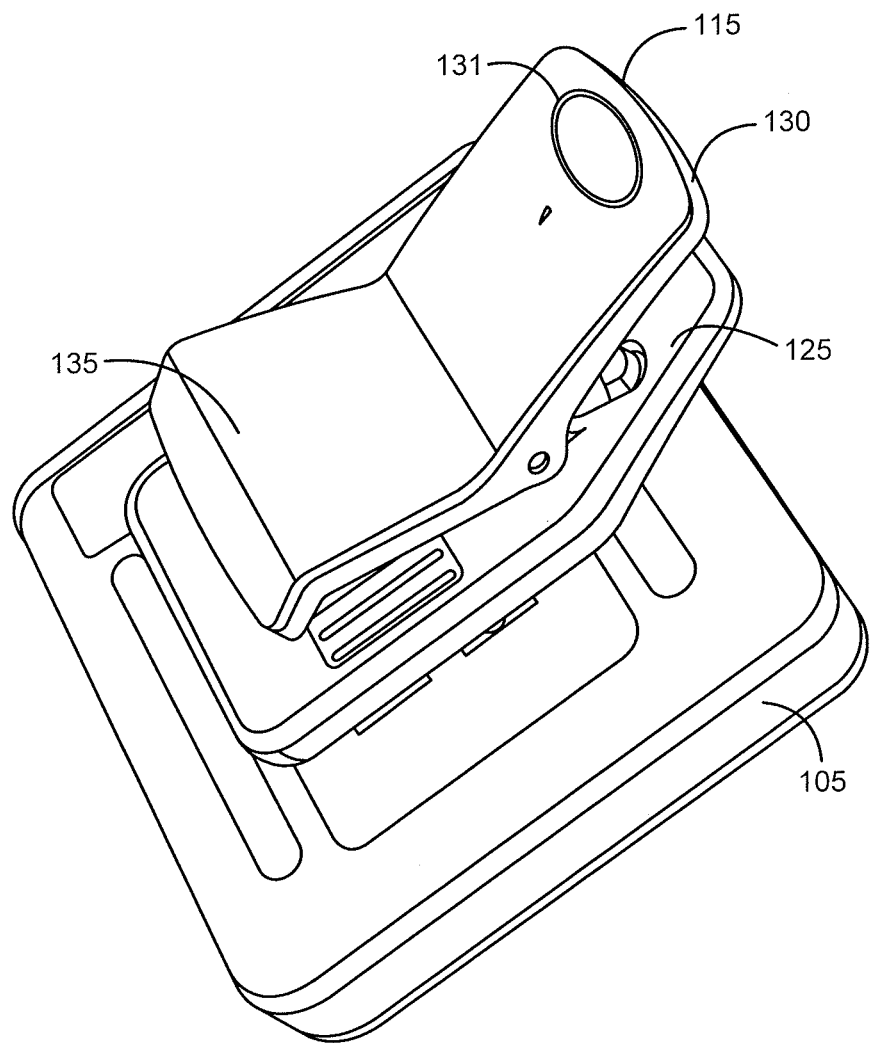
FIG. 3 is another view of a patient monitoring pod attached to a clip.

FIG. 3 is another view of a patient monitoring pod 105 attached to a clip 115. The view shown in FIG. 3 is from the top of the clip 115 towards the patient monitoring pod 105. The clamp 135 is seen above the base portion 125 of the clip. The lever arm 130 is connected to the clamp, and an ergonomic feature 131 is located at the end of lever arm 130 to help a user to hold on to the clip while applying pressure to the lever arm 130.

Figure 4:
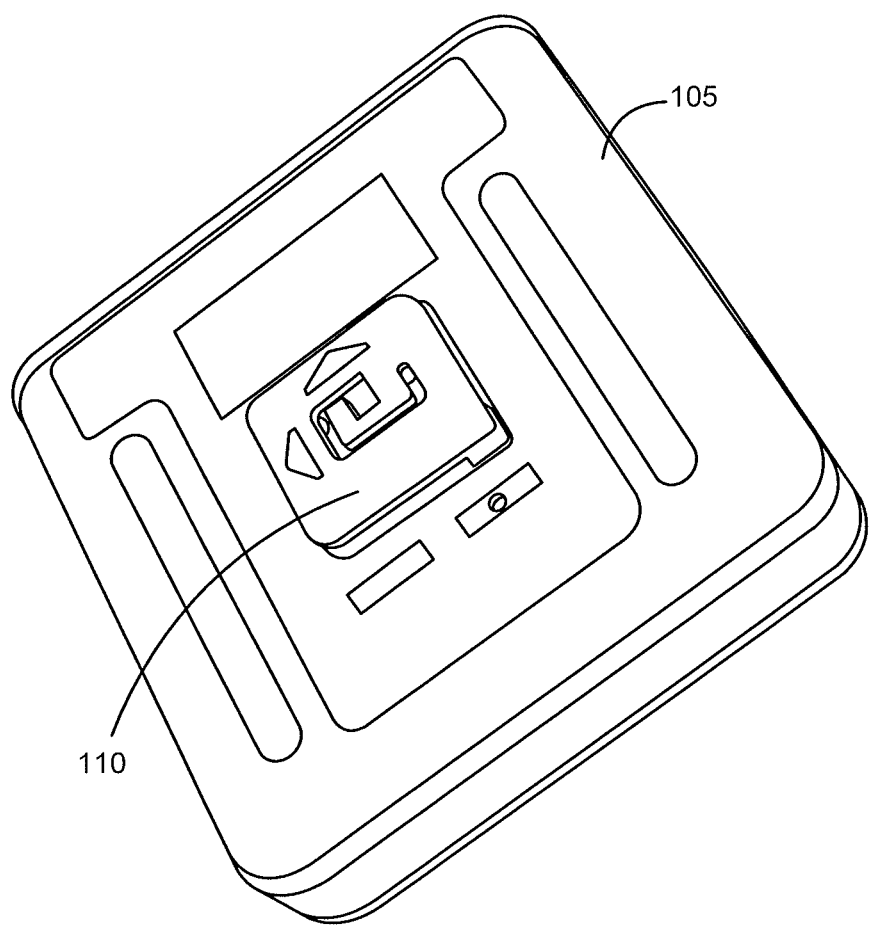
FIG. 4 illustrates another view of the patient monitoring pod shown in FIG. 1 without the clip attached.
Figure 5:
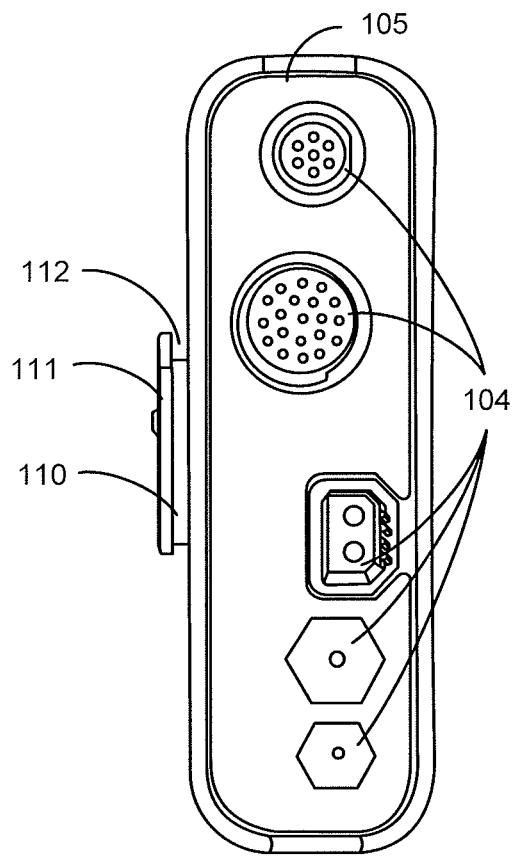
FIG. 5 illustrates a side view of a patient monitoring pod showing the connection ports or fittings.

FIG. 4 and FIG. 5 are alternate views of the patient monitoring pod 105. FIG. 4 illustrates another view of the patient monitoring pod 105 shown in FIG. 1 without the clip attached. The mount block 110 is shown as located in the middle of one of the square faces of the patient monitoring pod 105. FIG. 5 illustrates a side view of a patient monitoring pod 105 showing the connection ports or fittings 104 where cords or cables that communicate data to a patient monitoring device or that obtain readings from a patient attach. Also, the mount block 110 is visible, along with the interfacing portion 111 and the undercut 112. The types of reading that a patient monitoring pod can take include blood pressure, respiration rate, oxygen saturation, temperature, heart rate, and the like. The patient monitoring pod can be configured to interface with one or more sensors that can monitor a patient's blood pressure, respiration rate, oxygen saturation, temperature, heart rate, or any combination thereof.

Clip for Patient Monitoring Pod

Figure 6:
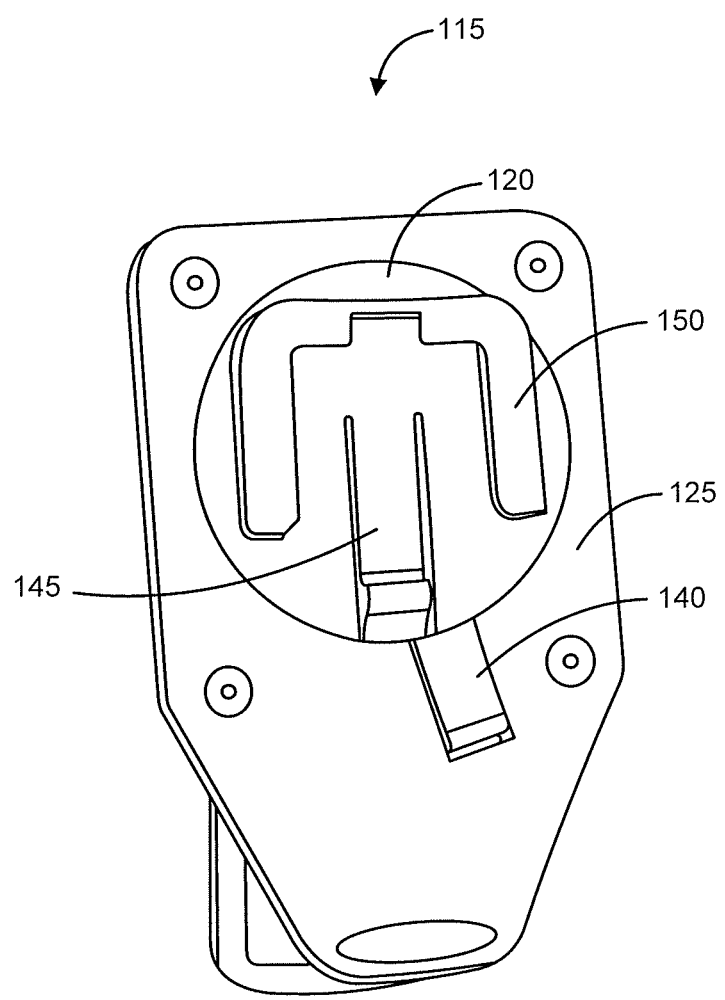
FIG. 6 illustrates a clip for a patient monitoring pod with a slide-on interface fitting.

FIG. 6 illustrates a clip 115 for a patient monitoring pod with a slide-on interface fitting 150. The base portion 125 includes the circular interface portion 120 that includes the slide-on interface fitting 150, and a locking mechanism 145. Also located on the base portion 125, and adjacent to the interface portion 120, is a lock release 140.

The clip 115 in FIG. 6 has a rotating interface portion 120. The slide-on interface fitting 150 with a locking mechanism 145 allows for a long-term connection between a clip 115 and a patient monitoring pod 105. When the mount block 110 (see FIG. 2) of the patient monitoring pod 105 slides into the slide-on interface fitting 150, the locking mechanism 145 depresses. When the mount block 110 is fully engaged in the slide-on interface fitting 150, the locking mechanism 145 springs into a position that holds the mount block 110 securely in the slide-on interface fitting 150. The locking mechanism 145 ensures that as the patient monitoring pod 105 rotates, such as when a user wants to change the direction in which the cords or cables emanate from the patient monitoring pod 105, the clip 115 will not come undone and disengage from the patient monitoring pod 105. The clip 115 allows the patient monitoring pod 105 to rotate and stay fixed in positions that are off-set by 90 degrees. To release the patient monitoring pod 105 from the clip 115, the clip 115 and patient monitoring pod 105 must be aligned such that the locking mechanism 145 is in a position to be depressed by the lock release 140 when a user actuates it.

Figure 7:
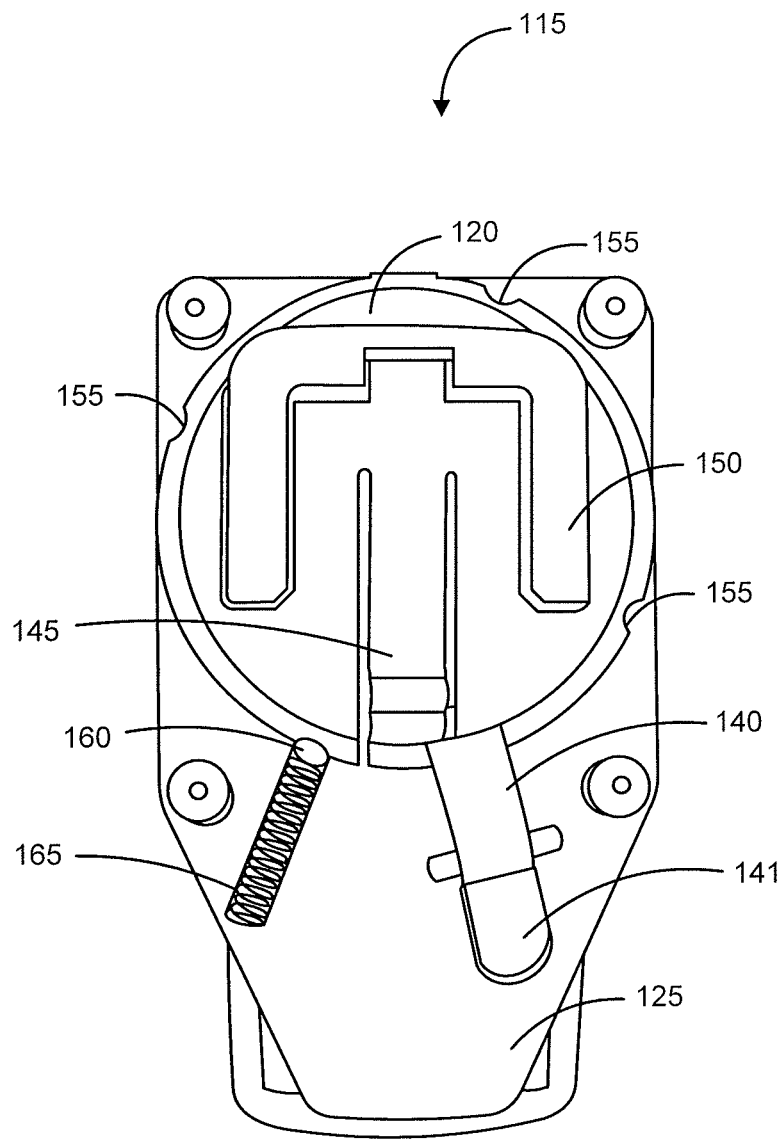
FIG. 7 illustrates a first view of the rotation and locking mechanisms in a clip for a with a slide-on interface fitting.

FIG. 7 illustrates a first view of the rotating interface 120 and locking mechanism 145 in a clip 115 for use with a slide-on interface fitting 150. FIG. 7 also displays the detents 155 in the interface 120 that cause the clip 115 and patient monitoring pod 105 to rotate and stay affixed relative to each other in 90 degree increments. To move the rotating interface 120, the patient monitoring pod 105 can be pushed in a direction with a force that can depress the ball 160 against the retaining spring 165 so that the ball is no longer settled into a detent 155. Once a suitable relative orientation between the patient monitoring pod 105 and the clip has been selected, a detent 155 accepts the ball 160 and the spring 165 ensures that the weight of the patient monitoring pod 105 and any cables or cords attached to it do not cause the relative position of the patient monitoring pod-clip assembly to change. When the user wishes to remove the clip 115 from the patient monitoring pod 105, the patient monitoring pod 105 can be pushed into a position wherein the locking mechanism 145 is aligned with the lock release 140. A button on the clip (not seen in FIG. 7, but shown on the reverse side of the base portion 125 in FIG. 9) can then be pushed, and the lock release actuator 141 actuates the lock release 140. At that point, the patient monitoring pod 105 can separate from the clip 115 because the mount block is free to slide out of the slide-on fitting 150. The ball 160 is shown as a sphere, but it can be buckyball shaped, a dodecahedron, shaped as a die with irregular faces, or any other suitable shape that allows for rotation of the rotating interface 120, as needed.

Figure 8:
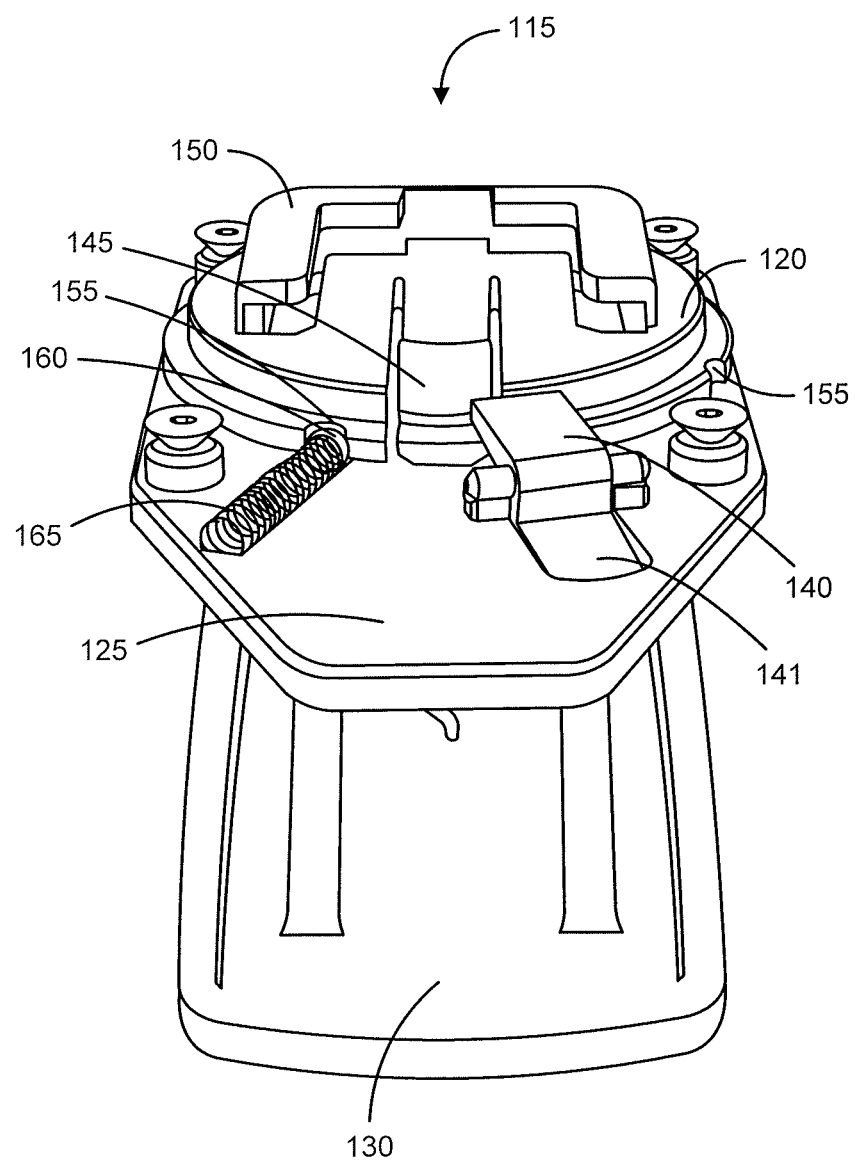
FIG. 8 illustrates a perspective view of the rotation and locking mechanisms in a clip for a with a slide-on interface fitting.

FIG. 8 illustrates a perspective view of the rotating interface 120 and locking mechanism 145 in a clip with a slide-on interface fitting 150. As in FIG. 7, the detents 155 on the rotating interface 120 and the ball 160 and spring 165 enable the clip 115 and patient monitoring pod 105 to maintain specific orientations relative to each other. The locking mechanism 145 enables the patient monitoring pod 105 to stay attached to the clip 115 during rotation. The lock release 140 and lock release actuator 141 will allow the patient monitoring pod 105 to slip out of the slide-on fitting 150 when properly aligned and actuated. The lever arm 130 can be seen in FIG. 8, and is pushed towards the base portion 125 when a user wishes to open the clamp 135 (not shown in FIG. 8).

Figure 9:
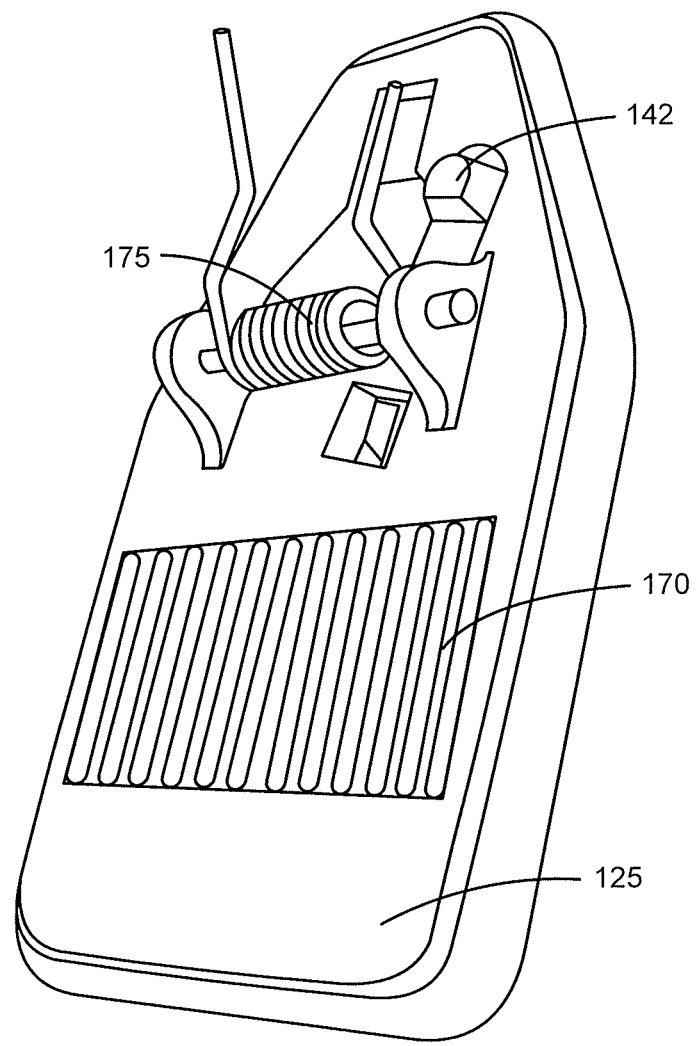
FIG. 9 illustrates a base portion with the lock release button for a clip with a slide-on interface fitting.

FIG. 9 illustrates a base portion 125 with the lock release button 142 for a clip 115 with a slide-on interface fitting 155 (shown in FIG. 8). Upon depressing the lock release button 142, the user activates the lock release actuator 141 (see FIG. 8) which in turn causes the lock release 140 to depress the locking mechanism 145, if properly aligned. FIG. 9 also illustrates the spring that imparts the clamping force of the clip 115 and a viscoelastic gripping surface 170. The viscoelastic gripping surface 170 can be complemented by another surface of a similar or different material on a facing portion of the clamp 135 (not shown in FIG. 9, but seen in FIG. 1). The ability to maintain a position on a pole, rod, or rail whether the clip 115 is oriented with the clamp 135 opening along a horizontal or vertical direction can be due in part to the increased grip from the viscoelastic gripping surface 170.

Figure 10:
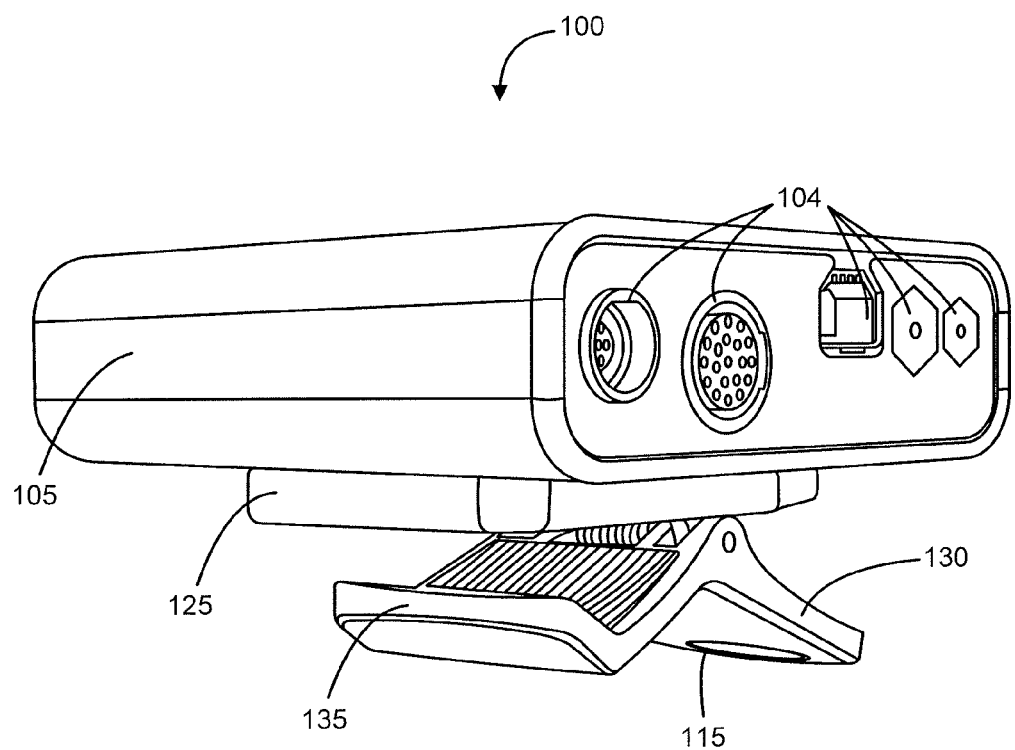
FIG. 10 illustrates a patient monitoring pod attached to a clip with a snap on interface fitting.

FIG. 10 illustrates a patient monitoring pod 105 attached to a clip 115 with a snap on interface fitting. In some implementations, there can be less discernible space between the clip 115 and the patient monitoring pod 105 in FIG. 10 than is shown in FIG. 1. That is because the interface on the base portion 125 of the clip 115 shown in FIG. 10 is recessed. The clip 115 of FIG. 10 also has a clamp 135 and a lever arm 130. The viscoelastic gripping surface 170 on the inner portion of the clamp 135 is shown in FIG. 10, as are the connection ports or fittings 104.

Figure 11:
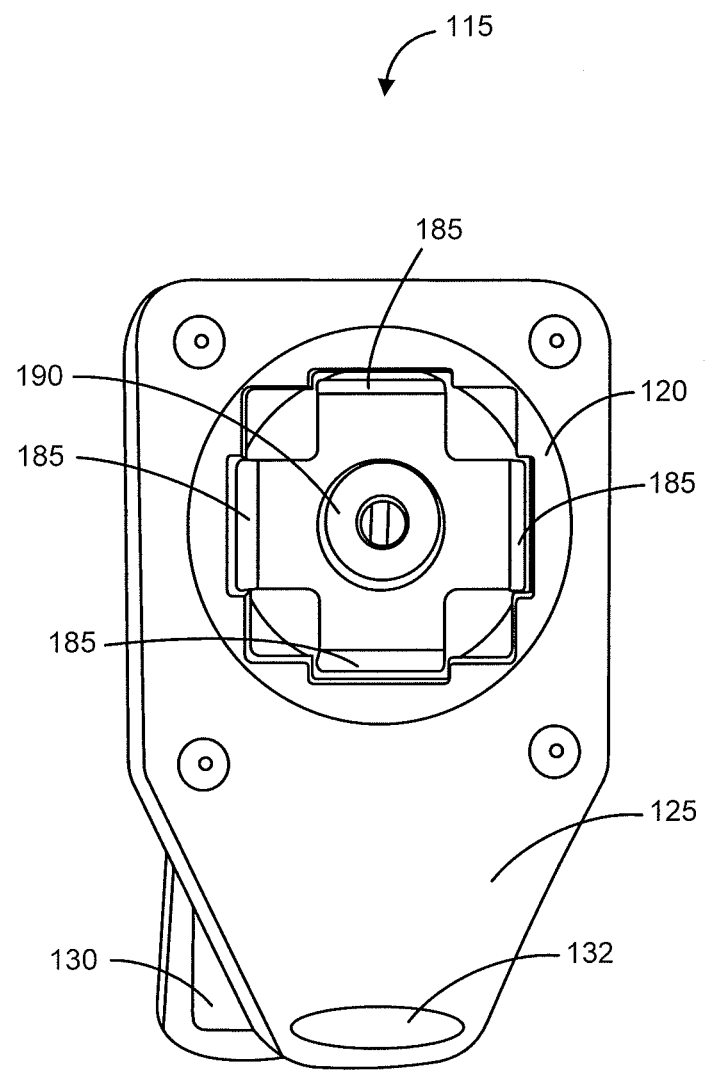
FIG. 11 illustrates a clip with a snap on interface fitting.

FIG. 11 illustrates a clip 115 with a snap on interface fitting. The snap on interface fitting includes tension springs 185 and a rivet 190. The interface 120 is a rotating interface and spins about the rivet 190 which extends through the base portion 125. As in the clip 115 shown in FIG. 6, a user may rotate the clip 115 relative to the patient monitoring pod 105 such that the patient monitoring pod will stay affixed in 90 degree increments. The tension springs 185 maintain the mount block 110 (shown in FIG. 2) within the recessed snap on fitting. In this way, a user can have a short-term connection between the clip 115 and patient monitoring pod 105. Because of the short-term nature of the connection between the clip 115 and patient monitoring pod 105, there is no locking mechanism in the clip 115. Also shown in FIG. 11 is the lever arm 130 and an ergonomic feature 132 on the base portion 125. The ergonomic feature 132 can help a user to better grasp the base portion 125 when using the clip 115.

Figure 12:
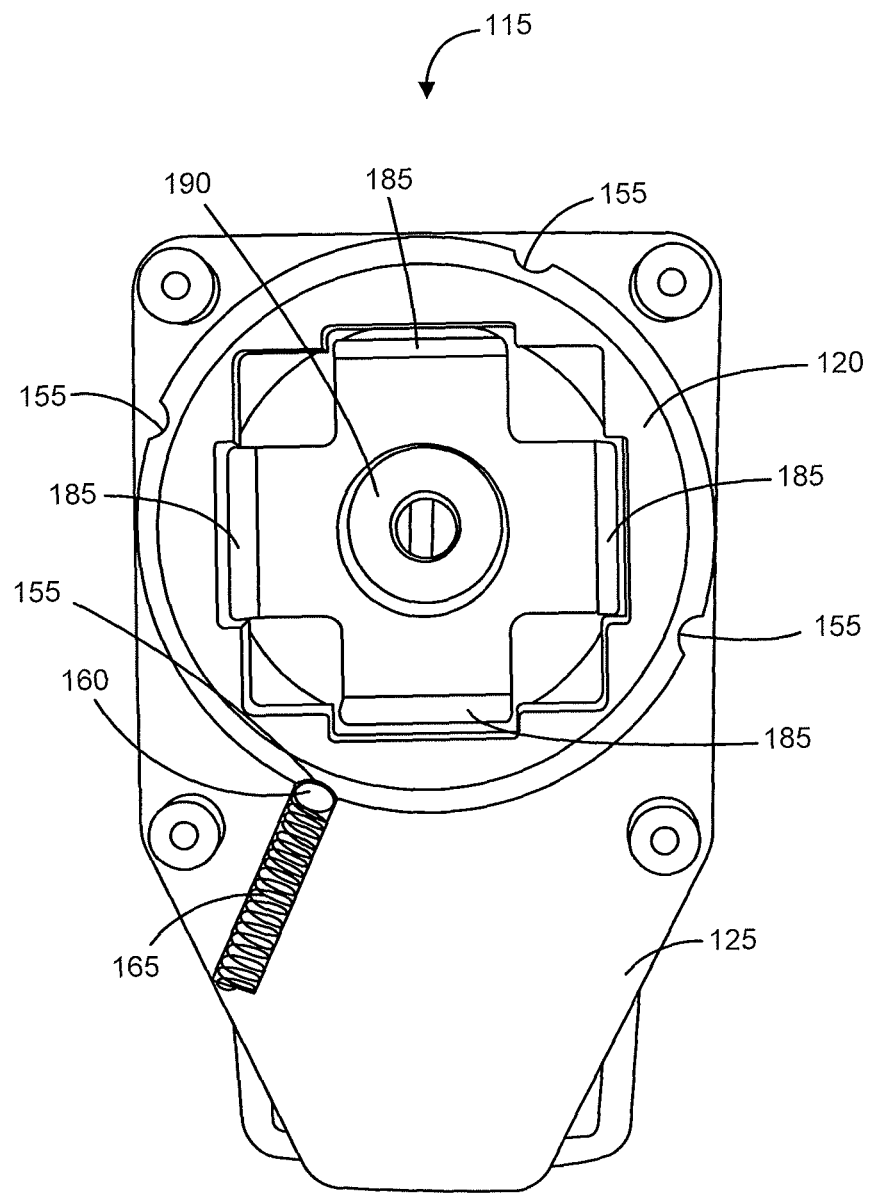
FIG. 12 illustrates the rotation mechanism for a clip with a snap on interface fitting.
Figure 13:
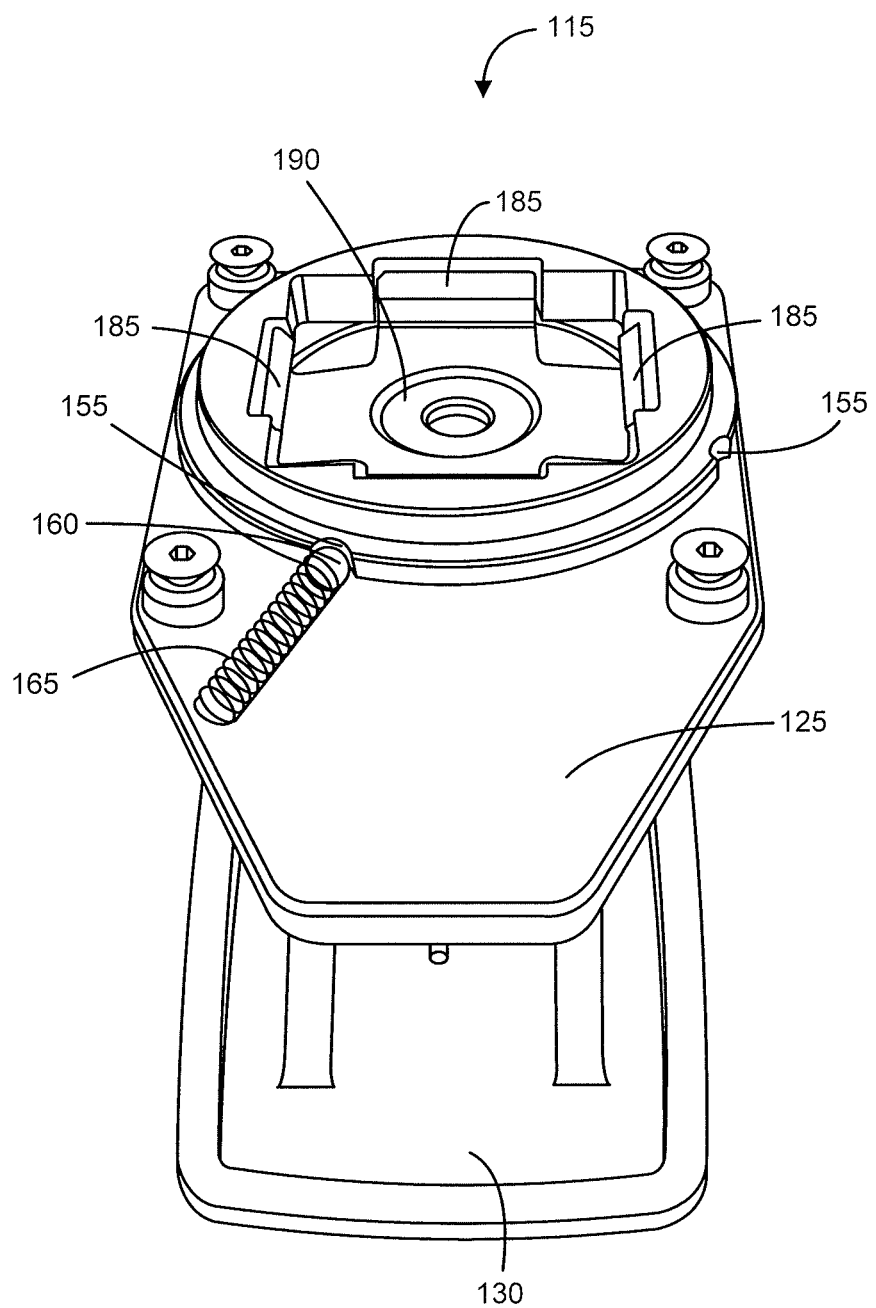
FIG. 13 is a perspective view of the rotation mechanism for a clip with a snap on interface fitting.

FIGS. 12 and 13 illustrate the rotation mechanism for a clip 115 with a snap on interface fitting. The rotating interface 120 has detents 155 which help maintain the relative position of the clip 115 and the patient monitoring pod 105. The detents 155 receive the ball 160 that is pressed upon by the spring 165 to resist motion of the clip-patient monitoring pod assembly. The spring 165 exerts sufficient pressure on the ball 160 to support the patient monitoring pod 105 with cables and cords attached. The rivet 190 allows the interface 120 to rotate, and the tension springs 185 maintain the connection to the mount block 110 (see FIG. 2).

Figure 14:
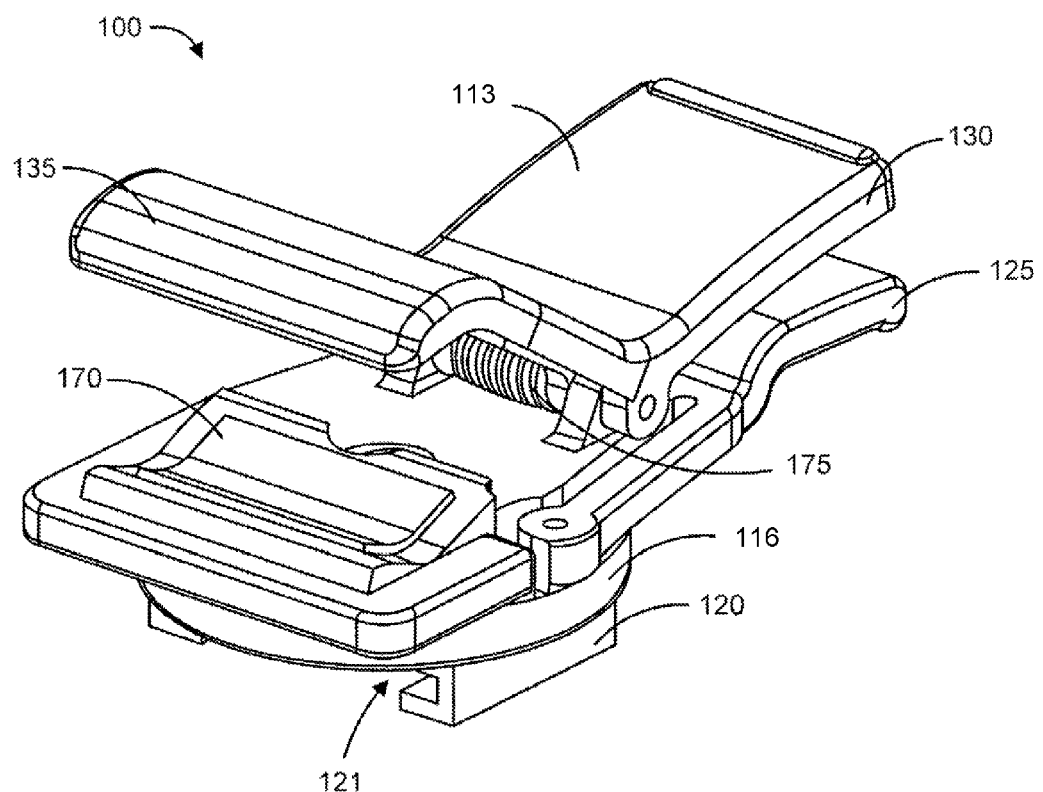
FIG. 14 shows an exemplary clip for attaching a patient monitoring pod to a rod, pole, stand, or patient monitoring device.

FIG. 14 shows an exemplary clip 100 for attaching a patient monitoring pod to any of a fixed or moveable structure, as described above. The clip 100 includes a clip base 125, a lever arm 130, a user grasping area 113, a clamp 135, friction pads 170, a torsion spring 175, a latch base 116, and an interface 120.

The lever arm 130 has the user grasping area 113 at one end and the clamp 135 at the other end. Between the user grasping area 113 and the clamp 135 is the torsion spring 175. The torsion spring 175 is located between the lever arm and the clip base 125. The configuration of the torsion spring 175 applies force to the lever arm 130 and the clip base 125 such that the clamp 135 on the lever arm 130 is biased towards the clip base. The torsion spring 175 can be shaped in any suitable manner to cause the biasing of the clamp 135 towards the clip base 125. FIG. 14 shows the torsion spring 175 has having a tight, cylindrical coil of material.

A user can increase the distance between the clamp 135 and the clip base 125 by pushing or squeezing the user grasping area 113 towards the clip base 125. The clamp 135 section of the lever arm 130 can include a friction pad (not shown in this view) that is located facing another friction pad 170 that is located on the clip base 125. The one or more friction pads 170 can help the clip 100 to maintain a given position on a surface, such as a rod, a rail, a patient monitoring device, a shelf, and the like, by increasing the frictional force between the surface and the clip 100.

Attached to the clip base 125 is a latch base 116, as shown in FIG. 14. The latch base 116 is shown as a disk with one side towards the clip base 125 and its second side towards the interface 120. The interface 120 has a receiving slot 121, into which a component on a monitoring pod (not shown) can fit and be secured. The interface 120 can rotate when the clip is in an unlatched configuration and a user moves the latch base 116. The latch base 116 can rotate and lock into a latched configuration at fixed intervals, or the latch base 116 can rotate an arbitrary amount before a user locks the latch base 116 such that the clip 100 is in a latched configuration.

The interface 120 can be an interface for attaching any suitable monitoring pod in either a slide fitting or a push fitting. The interface 120 can allow the user to attach the monitoring pod in more than one configuration. The combination of the rotational abilities of the latch base 116 and the different permutations of attachment of the clip 100 to the patient monitoring pod can allow the user to obtain a suitable configuration that allows comfort of the patient and access of a caregiver, or other user, to all of the cables or leads to and from the patient monitoring pod.

Figure 15:
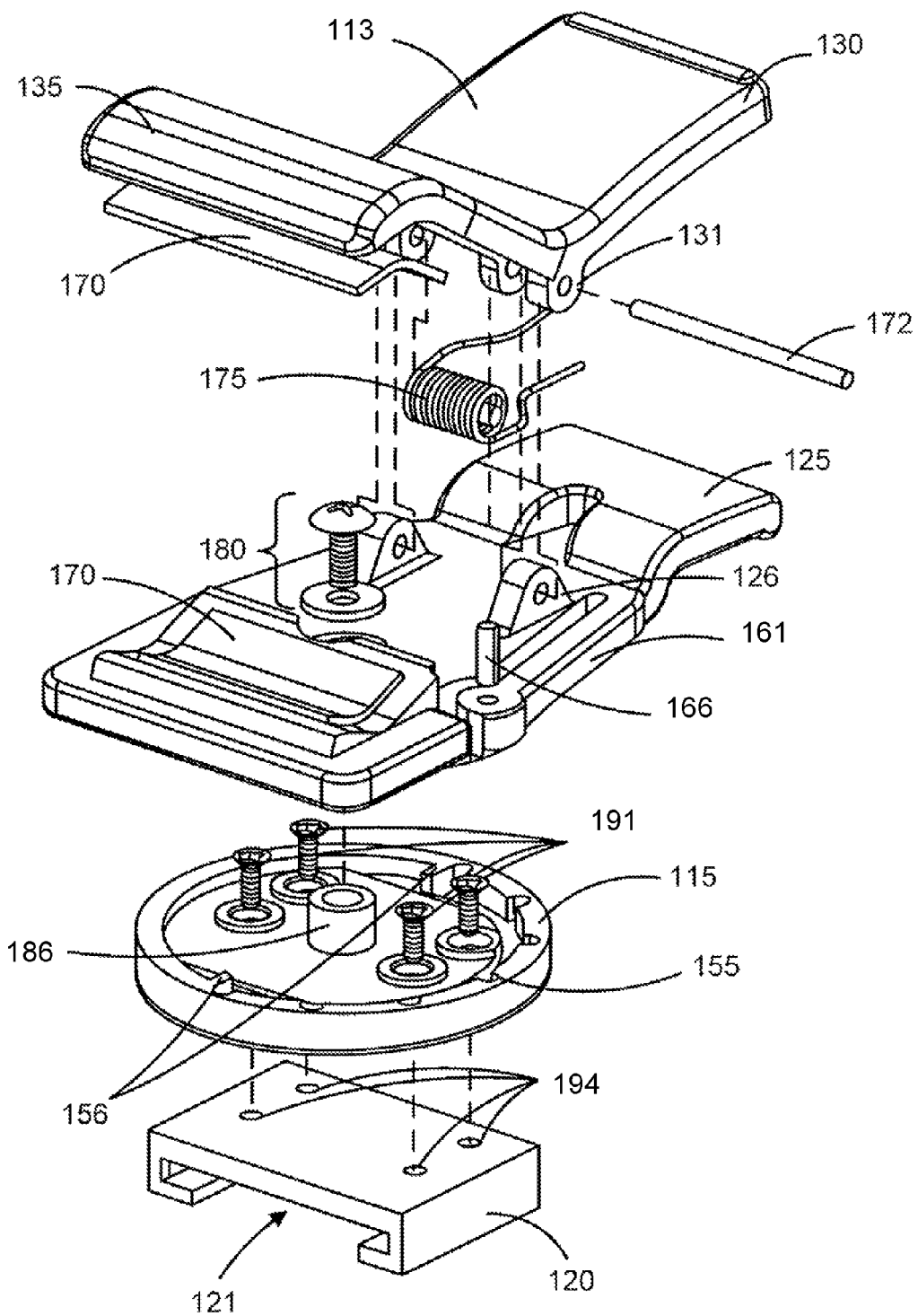
FIG. 15 shows an exploded view of the exemplary clip in FIG. 14.

FIG. 15 shows an exploded view of the exemplary clip 100 of FIG. 14. In this exploded view, more components of the clip 100 can be seen. The clip 100 includes the lever arm 130, the user grasping area 110, the clamp 135, friction pads 170, the clip base 125, the torsion spring 175, the latch base 116, and the interface 120 with receiving slot 121, as shown in FIG. 14. The exploded view allows a better view of the following components: lever arm pivot points 133, a pivot mandrel 172, base pivot points 126, a latch arm 161, a latch pin 165, a rotation screw assembly 180, a screw receiving fitting 186 located on the latch base 116, notches 155 and rotation stops also located on the latch base 116, mounting block attaching screws 190, and screw holes 194. In FIG. 15, the friction pad 170 on the lever arm 130 at the clamp 135 end can be seen; this friction pad 170 was not visible in FIG. 14.

The torsion spring 175 attaches to the lever arm 130 and the clip base 125 via a pivot mandrel 172 that passes through the coil of material in the torsion spring 175. The pivot mandrel 172 also passes through the lever arm pivot points 133, as well as the base pivot points 126. The pivot points 133, 126 are the fulcrum about which the lever arm 130 moves as the user pushes or squeezes the user grasping area 113 of the lever arm 130 towards the clip base 125.

Additional features connected to the clip base 125 can be seen in FIG. 15. A rotation screw passes through a washer in the rotation screw assembly 180. The screw of the rotation screw assembly 180 also passes through the clip base 125 and attaches to a screw fitting 186 in the latch base 116. The rotation screw assembly 180 and the screw fitting 186 allow the clip base 125 to rotate relative to the latch base 116 into a convenient position for the user.

Mounting block attachment screws 190 pass through the latch base 116 and into screw holes 194 in the interface 120. The mounting block attachment screws 190 and screw holes 194 can be oriented such that only one configuration of the interface 120 is possible with respect to the latch base 116. Alternatively, the mounting block attachment screws 190 and screw holes 194 can be oriented such that more than one configuration of the interface 120 is possible with respect to the latch base 116, such as two or three configurations.

A latch arm 161 that is attached at one end to the clip base 125 is shown with a latch pin 165 that extends through the end of the latch arm 161 that is free of the clip base 125. The end of the latch arm 161 that surrounds the latch pin 165 can be shaped to be of a greater width than the rest of the latch arm. The clip base 125 can be shaped to accept the latch arm 161 when the user pushes the latch arm 161 towards the central portion of the clip base 125.

The latch arm 161 is separated from the central portion of the clip base by a space, slot, or trough of a width that can be equal to the width of the latch arm 161, but is usually equal to the distance required to allow transition of the clip 100 from a latched configuration to an unlatched configuration, as defined by the position of the latch pin 165 with respect to the notches 155 on the latch base 116. The latch arm 161 is rigid enough to withstand the user pushing in against it. The material from which the latch arm 161 is made can be the same as that of the clip base 125, or the material of the latch arm 161 can be different from that of the clip base 125.

The latch base 116 has a screw fitting 186 into which the screw of the rotation screw assembly 180 fits. The screw fitting 186 can be substantially in the center of the latch base 116, or if desired, the screw fitting 186 can be off-centered. Along the periphery of the latch base 116 are notches 155. The notches 155 can be evenly spaced, such as at 30° intervals, 15° intervals, 45° intervals, or any other suitable interval. Adjacent to the notches 155 is a ring, either a partial ring or a whole ring, that allows for movement of the latch pin 165 out of any given notch or from one notch into another notch. The ring will have a width greater than or equal to the diameter of the latch pin 165. The notches 155 can be any suitable shape to immobilize the latch pin 165, such as having a cross-sectional area that resembles a semi-circle with a radius equal to or greater than that of the latch pin 165.

The notches 155 can be placed along only a portion of the periphery of the latch base 116, as shown in FIG. 15, or the notches 155 can be located along the entire periphery of the latch base 116, such that a 360° rotation is possible. The rotation of the latch base 116 can be restricted by rotations stops 156. The rotation stops 156 can be placed to limit rotation of the latch base 116, such as to a finite range such as 180°, 90°, 270°, 200°, and the like.

Figure 16:
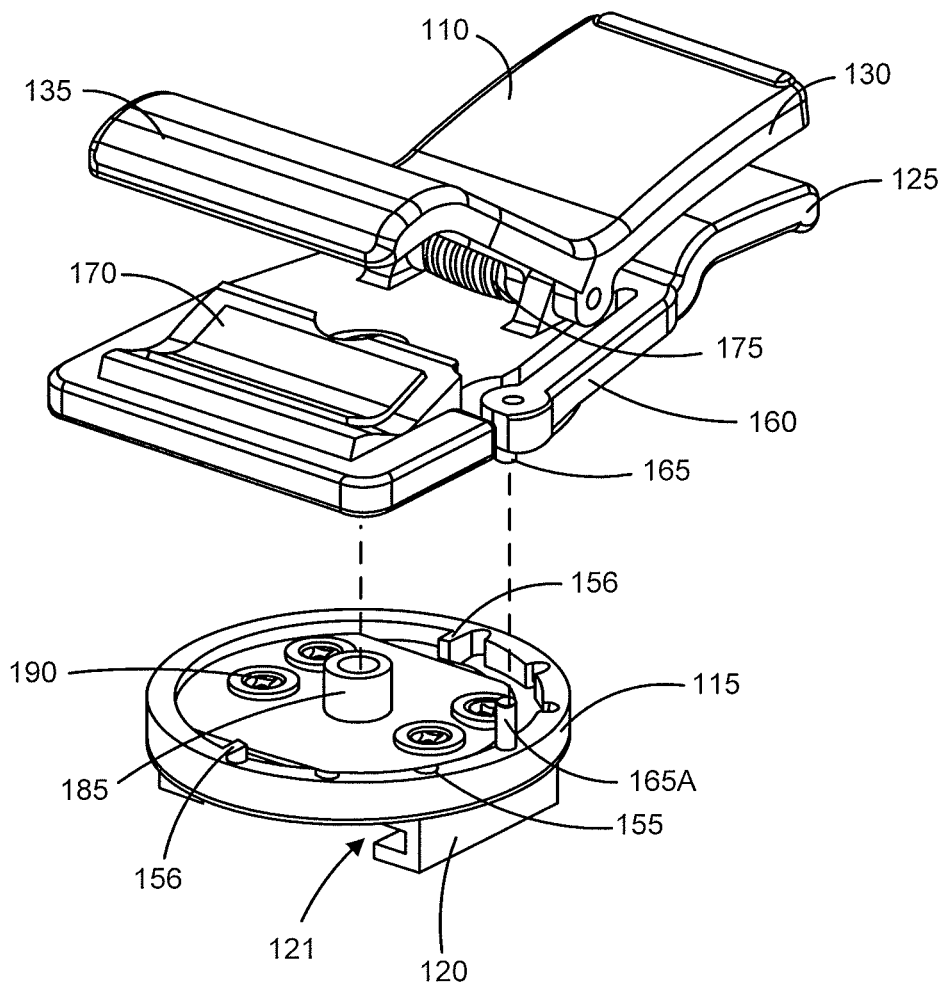
FIG. 16 is a view of the exemplary clip of FIG. 14 in a latched position.

FIG. 16 shows the exemplary clip 100 in a latched configuration. In addition to the components shown in FIG. 14 and FIG. 15, the latch pin 165 is shown in a position 165A that seats the latch pin 165 into a notch 155. When the latch pin 165 is in a seated position 165A, the latch base 116 cannot rotate.

Figure 17:
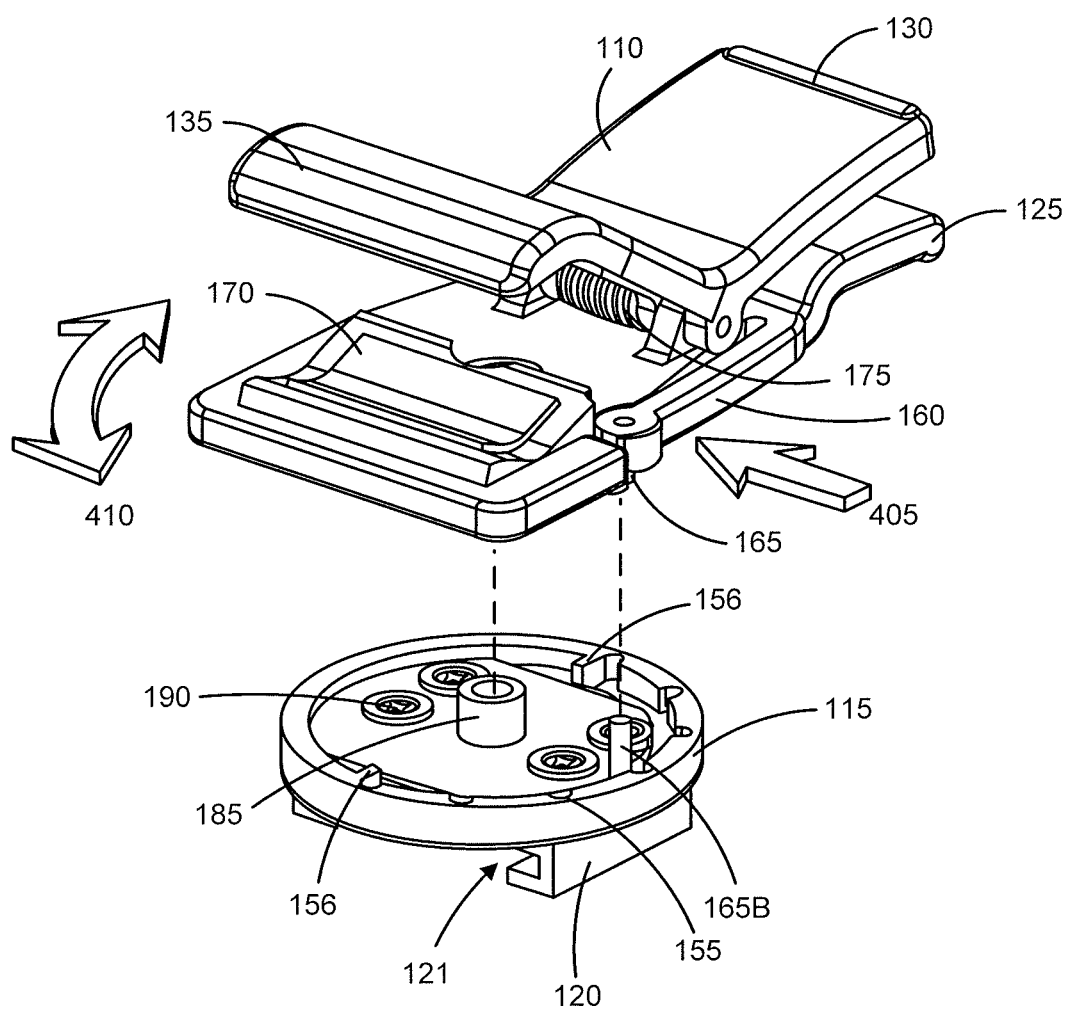
FIG. 17 is a view of the exemplary clip of FIG. 14 in an unlatched position.

FIG. 17 shows the exemplary clip 100 in an unlatched configuration. The clip 100, as shown, includes all of the components described with respect to FIG. 14 and FIG. 15. In addition to these components, FIG. 17 shows the latch pin 165 in a released position 165B. The latch pin 165 is shown located in the ring of the latch base 116 when it is in the released position 165B. To achieve this released position 165B, the user applies a force 405 on the latch arm 161. The force 405 causes the latch arm 161 to move towards the center portion of the clip base 125, and moves the latch pin 165 out of the notch 155 that it was in, into the ring and the released position 165B.

From here, the released position 165B, the latch pin 165 does not impede the rotation of the latch base 116 when the user applies a rotational force 410. Once the user has determined an optimal position for the clip 100 relative to the patient monitoring pod that is attached, or will be attached, to the interface 120, the user releases the force 405 on the latch arm 161. The latch pin 165 can then assume the latched position 165A, shown in FIG. 16.

The components of the clip, including the base, lever arm, and clamp, can be any suitable shape to allow an attached medical device to rotate with respect to the clip and to exert enough force to attach a medical device connected to the clip to a shelf, rail, or other structure. The base portion 125 can be a plate, an arch, a partial sphere, or any other suitable shape to allow rotation of a medical device about the clip.

Patient Monitoring Pods for Use in Arrays or Stacks

Figure 18:
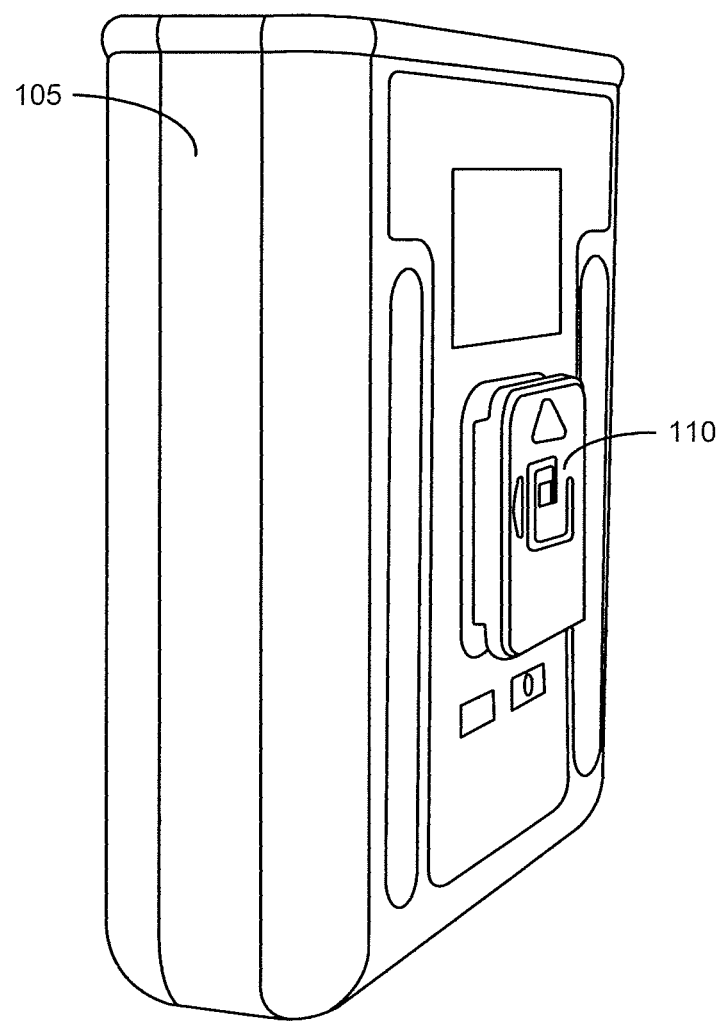
FIG. 18 illustrates a patient monitoring pod with a mount block for fitting into a clip; a fitting to attach to a shelf, bar, or pole; or a recessed fitting on another patient monitoring pod.
Figure 19:
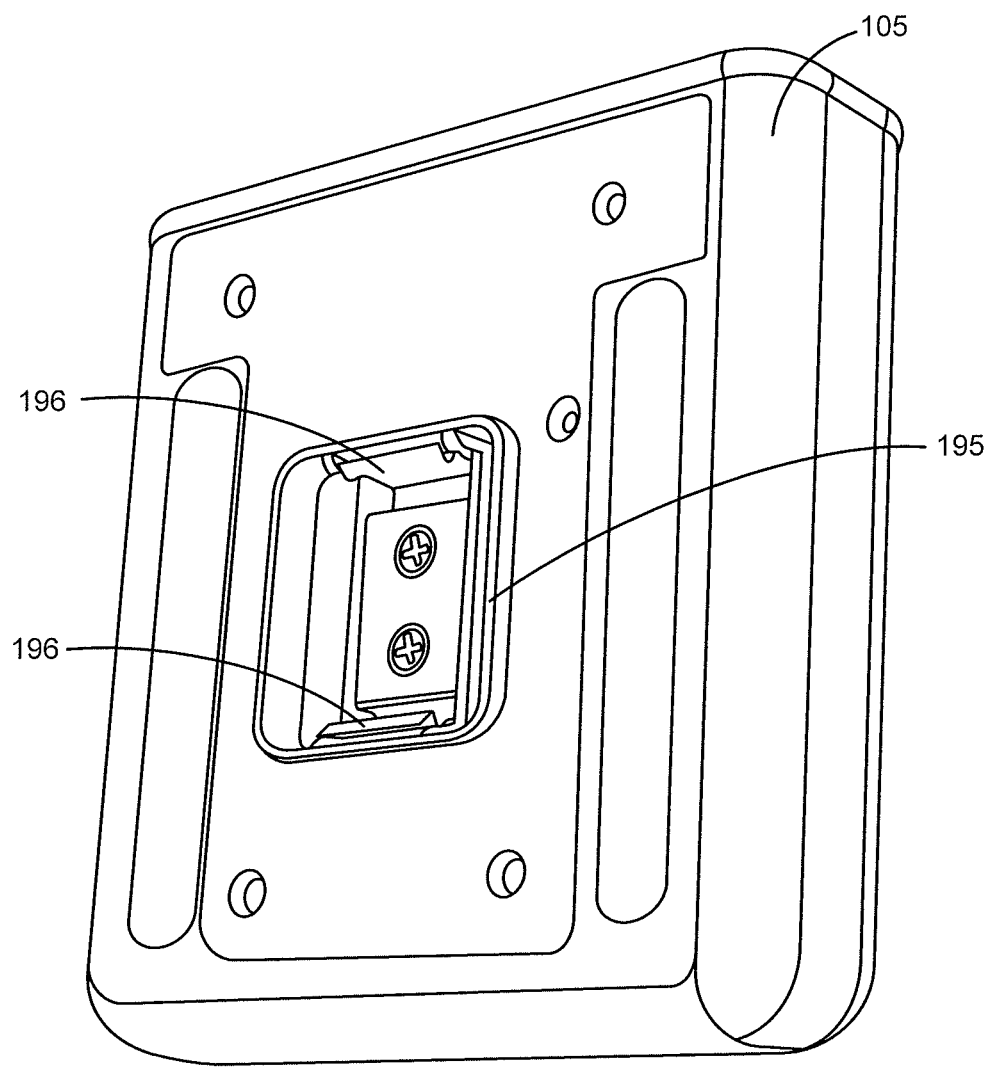
FIG. 19 illustrates another view of the patient monitoring pod shown in FIG. 18 with a recess fitting to receive a mount block on another patient monitoring pod.

FIGS. 18 and 19 show two sides of a patient monitoring pod 105 that can attach to a clip 115; a fitting to attach to a shelf, bar, or pole; or a recessed fitting on another patient monitoring pod via a mount block 110. The recessed fitting 195 on another patient monitoring pod 105 can include two or more tension springs 196 that keep the mount block 110 within the recessed fitting 195 until a user exerts sufficient energy to separate the mount block 110 and recessed fitting 195.

Patient monitoring pods 105 configured in this way can be stacked one atop another so long as each patient monitoring pod 105 has a mount block 110 on one face and a recessed fitting 195 on a face parallel to the first face. Patient monitoring pods 105 that are not of similar size can still be stacked as long as each patient monitoring pod 105 has the same relative location (i.e., on opposing faces) of the mount block 110 and recessed fitting 195. This configuration can be useful when clips 115 are scarce or when transporting numerous patient monitoring pods 105 associated with a single patient. When transporting a patient and numerous patient monitoring pods 105, keeping the pods and cords in the same orientation can reduce the amount of time a caregiver needs to spend "breaking-down" or removing a patient from a first location and "setting-up" or installing the patient in a second, new location. Additionally, this can enable patient monitoring to continue while the patient is in transit between the first and second location.

Methods of Patient Monitoring

The patient monitoring pods and clips and systems described herein in various implementations can be used with a patient monitoring device to monitor the condition of a patient, both while a patient is stationary and while a patient is in transit. In some implementations, a patient monitoring device can be set on a table or shelf next to a patient and one or more patient diagnostic modules can be attached to the patient monitoring device in a way that data and power is transmitted between the patient diagnostic modules and the monitoring device. The patient monitoring device can be seated in a dock on that is on a table, shelf, medical stand, or in a cabinet in other implementations. Additionally, in other implementations, the patient monitoring device can hang from a rail or edge of a patient's bed or gurney, free from a dock. In some implementations, a patient monitoring device can be in a dock when a patient is in a first location, then the monitoring device can be on a shelf, rail, bed or other structure that may move with a patient, and then be in a dock again as needed to transfer data and/or power between the patient monitoring device and dock. In such implementations, the patient monitoring pods can be attached to the patient monitoring device via a clip, or the patient monitoring pods can be stacked beside the patient monitoring device in an interlocking manner, or the patient monitoring pods can be attached to a nearby rail, stand, or pole using a clip as described herein. Rotation of the latch base of the clip can occur prior to after attachment of a patient monitoring pod to the clip.

The clip for a patient monitoring pod has a design that includes a base plate with an interface portion on one side and a clamp attached to a lever arm on the opposed side. The base plate and lever arm have ergonomic features that can allow a user to better utilize the clip. The design of the clip for a patient monitoring pod described herein is more fully described in U.S. Design patent application No. 29/427,118, titled "Clip For a Patient Monitoring Pod," filed 13, Jul. 2012. This application, U.S. Design patent application No. 29/427,118, is hereby incorporated by reference herein in its entirety.

The foregoing description describes clips in use primarily with patient monitoring pods, however, such clips can also be used with other devices, including medical devices, electrical equipment, support devices, routing conduits and apparatus, and other devices or apparatus that can suitably attach to the described clips.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows and steps for use described herein do not require the particular order shown, or sequential order, to achieve desirable results. Similarly, elements located on the front, back, side, top, or bottom of an embodiment or implementation are to be understood as relatively positioned. Other embodiments can be within the scope of the claim.

What is claimed is:

1. A clip for attaching a medical device to a structure, comprising:
    a base portion;
    a rotating interface portion rotatably connected to the base portion and comprising:
        an interface fitting to interface with the medical device, the interface fitting operably connected to the rotating interface portion;
        a locking mechanism to lock the interface fitting to the medical device; and
    a lever arm connected with the base portion, the lever arm having:
        a user grasping area,
        a clamp, and
        a torsion spring that provides torsion to the connection with the base portion;
    wherein the base portion has a lock release to release the locking mechanism from the medical device.

2. The clip of claim 1, wherein the interface fitting is a sliding interface fitting.

3. The clip of claim 1, wherein the interface fitting is a snap on fitting.

4. The clip of claim 1, further comprising one or more friction pads.

5. The clip of claim 4, wherein the one or more friction pads are located on opposed, facing portions of the clamp, at a portion of the clamp that is configured to contact the structure.

6. The clip of claim 1, wherein the structure comprises a shelf, a rod, a bed, or any combination thereof.

7. The clip of claim 1, further comprising a rotation mechanism that allows the rotating interface portion to rotate on the base portion, the rotation mechanism comprising at least one ball, a spring, and at least one detent.

8. The clip of claim 1, further comprising a rotation mechanism that allows the rotating interface portion to rotate on the base portion, the rotation mechanism comprising a latch arm and a latch pin.

9. The clip of claim 1, wherein the clip is configured to rotate in discrete increments.

10. The clip of claim 1, wherein the clip is configured to rotate in any convenient amount.

11. The clip of claim 1, wherein the locking mechanism is configured to release the medical device only when the rotating interface portion is in a specific position with respect to the clip base portion.

12. The clip of claim 1, wherein the base portion is a plate.

13. A method, comprising:
    providing a patient monitoring pod and clip assembly comprising:
        patient monitoring pod; and
        a clip configured to releasably connect to the patient monitoring pod, the clip comprising:
            a base portion;
            a rotating interface portion rotatably connected to the base portion and comprising:
                an interface fitting to interface with the medical device, the interface fitting operably connected to the rotating interface portion;
                a locking mechanism to lock the interface fitting to the medical device; and
            a lever arm connected with the base portion, the lever arm having:
                a user grasping area,
                a clamp, and
                a torsion spring that provides torsion to the connection with the base portion; and
    providing physiological sensors configured to be attached to a patient and configured to provide data to the patient monitoring pod and to monitor the patient's blood pressure, respiration rate, oxygen saturation, temperature, heart rate, or any combination thereof;
    wherein the base portion has a lock release to release the locking mechanism from the medical device.

14. A clip for attaching a medical device to a structure, comprising:
    a lever arm comprising a user grasping area and a clamp;
    a base portion in a position opposed to the lever arm and connected to the lever arm via a torsion spring;
    a rotation mechanism configured to restrict rotation of the base portion with respect to the medical device, the rotation mechanism comprising:
        a latch arm attached at first end to the base portion and free at second end;
        a latch pin configured to sit in the second end of the latch arm; and
        a latch base operably connected to the base portion, the latch base configured to accept the latch pin; and
    an interface fitting to interface with the medical device and operably connected to the latch base of the rotation mechanism;
    wherein the torsion spring provides torsion between the lever arm and the base portion.

15. The clip of claim 14, wherein the latch base comprises notches, the notches configured to allow for immobilization of the latch pin and movement of the latch pin in and out of each notch.

16. The clip of claim 14, wherein the latch arm is configured to move the latch pin.

17. The clip of claim 14, wherein the latch arm is biased in a first configuration that prevents rotation of the latch base.

18. The clip of claim 14, wherein the base portion is shaped to accept the latch arm when pressure applied by a user on the latch arm causes the latch arm to move towards the base portion.

19. The clip of claim 18, wherein moving the latch arm towards the base portion allows for rotation of the latch base.

20. The clip of claim 18, wherein moving the latch arm towards the base portion moves the latch pin into a position that does not impeded the rotation of the latch base.

* * * * *